(12) United States Patent
Lemoine et al.

(10) Patent No.: US 7,306,577 B2
(45) Date of Patent: Dec. 11, 2007

(54) LOW-NOISE VACUUM RELEASE SUCTION DEVICE AND CONTROLLABLE ASPIRATOR USING SAME

(76) Inventors: Patrick D. Lemoine, 906 Arnaud Avenue, Sept-Iles, Québec (CA) G4R 3C4; Maxime Bolduc, 4654 Gouin, Rock Forest, Québec (CA) J1N 2C5; Martin Brouillette, 1580 John-Griffith, Sherbrooke, Québec (CA) J1J 4L4; Jean-Sébastien Plante, 477 Bouchette, Sherbrooke, Québec (CA) J1J 2T2

( * ) Notice: Subject to any disclaimer, the term of this patent is extended or adjusted under 35 U.S.C. 154(b) by 27 days.

(21) Appl. No.: 10/880,845

(22) Filed: Jun. 30, 2004

(65) Prior Publication Data

US 2005/0004520 A1 Jan. 6, 2005

(30) Foreign Application Priority Data

Jun. 30, 2003 (CA) .................................... 2433107

(51) Int. Cl.
*A61M 1/00* (2006.01)
(52) U.S. Cl. ....................................................... 604/118
(58) Field of Classification Search ........ 604/118–119, 604/121, 540, 541, 902, 283, 542, 91; 433/91, 433/92, 94, 95
See application file for complete search history.

(56) References Cited

U.S. PATENT DOCUMENTS

| | | | |
|---|---|---|---|
| 3,516,160 A | 6/1970 | Leffler | |
| 4,049,000 A | 9/1977 | Williams | |
| 4,221,220 A | 9/1980 | Hansen | |
| 4,522,592 A | 6/1985 | Johnson | |
| 4,534,542 A | 8/1985 | Russo | |
| 4,729,765 A * | 3/1988 | Eckels et al. ............... | 604/540 |
| 5,013,300 A | 5/1991 | Williams | |
| 5,195,952 A * | 3/1993 | Solnit et al. .................. | 604/19 |
| 5,401,255 A | 3/1995 | Sutherland et al. | |

(Continued)

FOREIGN PATENT DOCUMENTS

CA 2042523 11/1991

OTHER PUBLICATIONS

Mossman et al., "An Experimental Investigation of the Design Variables for NACA Submerged Duct Entrances," National Advisory Committee for Aeronautics, Washington, D.C. NACA RM No. A7I30 Jan. 8, 1948, 11 pages.

*Primary Examiner*—Nicholas Lucchesi
*Assistant Examiner*—Theodore J. Stigell
(74) *Attorney, Agent, or Firm*—Fay Kaplun & Marcin, LLP

(57) ABSTRACT

The present invention is concerned with a vacuum release suction device for regulating and controlling suction in an aspiration line, and which may be included in aspirators such as for example dentistry, surgery, or cosmetic tools. When operated, such tools generally generate noise which may become harmful to the tool user or for the patient on which the tool is used. More specifically, the suction device of the present invention includes a body having an inlet port and an outlet port defining a chamber in the body and a bypass inlet intersecting the chamber at an acute angle with respect to the longitudinal axis of the chamber, such that a main fluid stream is generated with minimized occurrences of flow separation, turbulence and therefore minimized generated aerodynamic noise.

31 Claims, 10 Drawing Sheets

U.S. PATENT DOCUMENTS

| | | |
|---|---|---|
| 5,425,637 A | 6/1995 | Whitehouse et al. |
| 5,496,268 A * | 3/1996 | Perla ........................... 604/27 |
| 5,509,802 A | 4/1996 | Whitehouse et al. |
| 5,542,929 A | 8/1996 | Laabs et al. |
| 5,730,727 A | 3/1998 | Russo |
| 5,855,562 A | 1/1999 | Moore et al. |
| 5,890,516 A * | 4/1999 | Talamonti ................... 137/605 |
| 5,899,884 A * | 5/1999 | Cover et al. ................. 604/119 |
| 5,964,733 A | 10/1999 | Laabs et al. |
| 5,975,897 A | 11/1999 | Propp et al. |
| 6,045,516 A | 4/2000 | Phelan |
| 6,074,208 A | 6/2000 | Mitchell |
| 2002/0108614 A1 | 8/2002 | Schultz |

\* cited by examiner

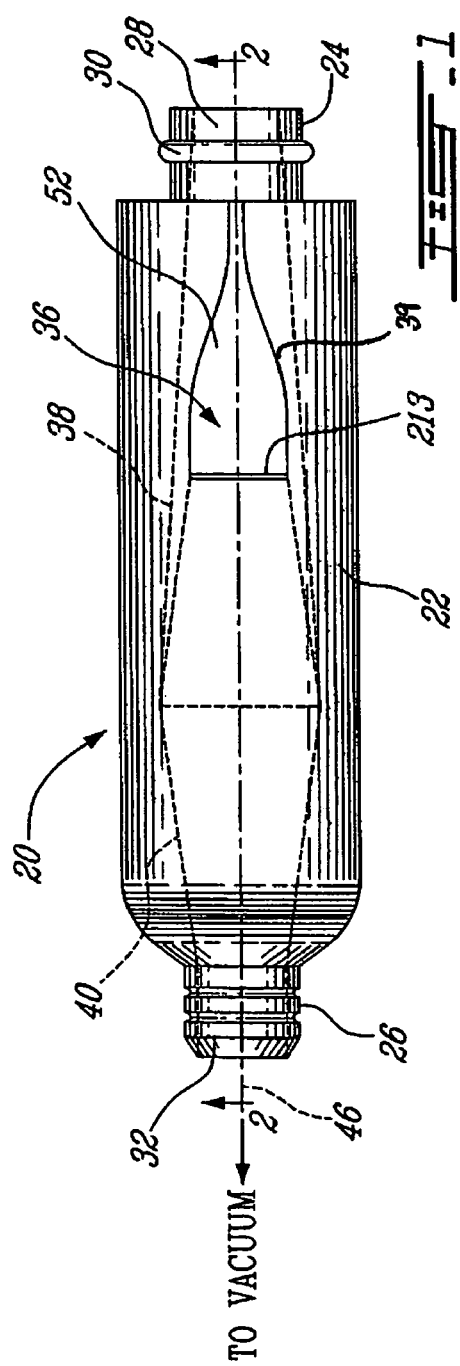

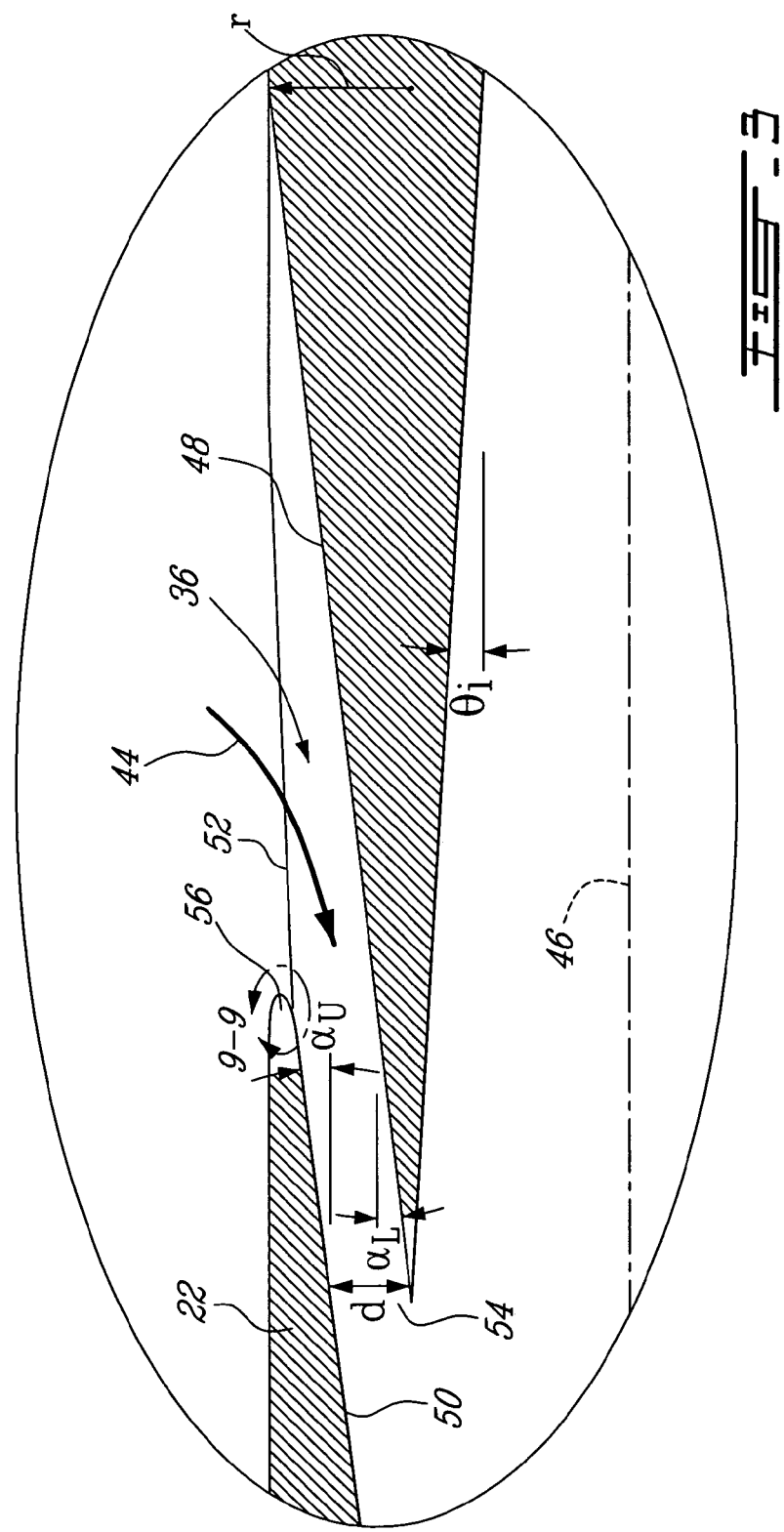

| X/L | 0 | 0.1 | 0.2 | 0.3 | 0.4 | 0.5 | 0.6 | 0.7 | 0.8 | 0.9 | 1.0 |
|---|---|---|---|---|---|---|---|---|---|---|---|
| $W/W_2$ | 1 | 0.994 | 0.914 | 0.764 | 0.614 | 0.466 | 0.390 | 0.314 | 0.236 | 0.160 | 0.084 |

| X | YU | YL |
|---|---|---|
| 0 | 0.197d | 0.197d |
| 0.125d | 0.087d | 0.325d |
| 0.250d | 0.056d | 0.375d |
| 0.375d | 0.036d | 0.412d |
| 0.500d | 0.021d | 0.440d |
| 0.625d | 0.012d | 0.462d |
| 0.750d | 0.006d | 0.481d |
| 0.875d | 0.002d | * |
| d | 0 | * |

* Merge with angle α

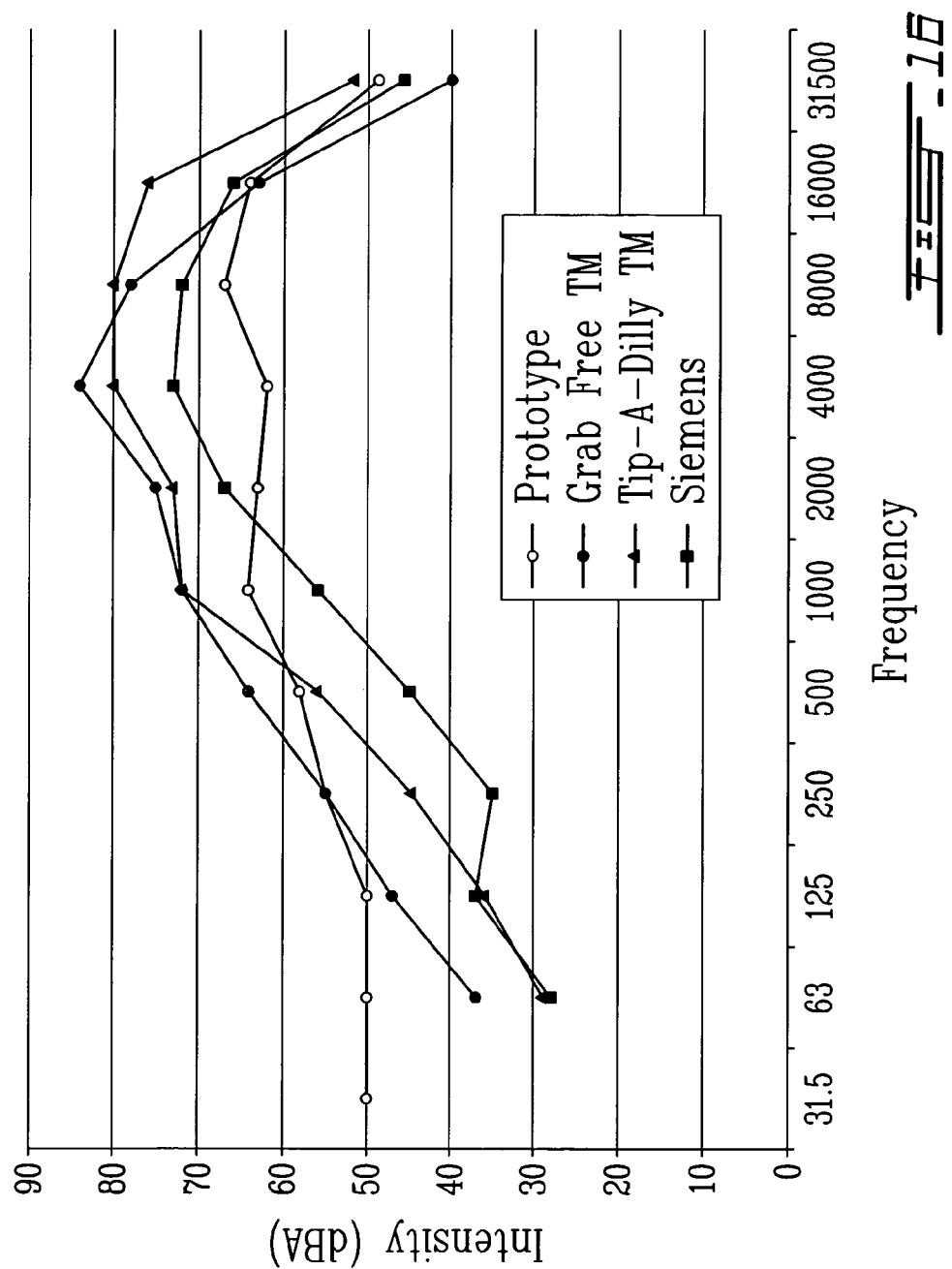

LOW-NOISE VACUUM RELEASE SUCTION DEVICE AND CONTROLLABLE ASPIRATOR USING SAME

FIELD OF THE INVENTION

The present invention generally relates to a suction device. More specifically, the present invention is concerned with a low noise vacuum release suction device and controllable aspirator using same.

BACKGROUND OF THE INVENTION

Aspirators connecting a vacuum source to a nozzle having a hollow tip are widely used in a plurality of professional fields and, namely, in the medical field. In dentistry, for instance, aspirators are used by dentists or hygienists and dental assistants for aspirating saliva, blood, water and debris from the patient's mouth during a treatment or surgery. The aspirating tool and the user thereof have to deal with opposite concerns in such an application.

Firstly, all liquid, solid particles and aerosols must be extracted in an effective manner, due to the health hazards they represent. The risks for the patient and the medical personnel tend to increase with the increasing use of high technology materials such as polymers and composites yielding toxic resin vapours and microscopic particles of silicium, quartz etc. when shaped with rotary instruments, cut, abraded or polished. These materials are often used for replacing silver amalgam fillings which, when deposited mechanically, produce toxic mercury vapours. Therefore, relatively strong suction and heavy airflow are desirable. However, contact of the aspirator tip aperture with the tongue or other delicate mouth tissues tends to block airflow, yielding a rapid negative pressure increase firmly grabbing the tissue against the aperture, and causing discomfort and risks of injury for the patient and stress both for the patient and the medical personnel. For that type of reasons, a vacuum release vent is now often provided on medical aspirators.

The vacuum release vent is generally an auxiliary bypass orifice, smaller than the main suction port, provided along the aspirating line, which enables penetration of air into the suction line with some restriction when air intake is obstructed at the main port, thus preventing vacuum inrush and water hammer effects. An early design of such a vented aspirator is described in U.S. Pat. No. 3,516,160 issued to Leffler in June 1970, which introduces the Tip-A-Dilly™ aspirator 100 illustrated in FIG. 4 of the appended drawings. The aspirator 100 includes a body 103 provided with two bypass orifices 101, 102 and terminated at its upstream end by a portion 105 provided with a main inlet bore 107 connected to a suction tip 106, and at its downstream end by an outlet portion 104 for connection to a vacuum hose. In operation, when vacuum is applied at outlet 104, a fluid stream 108, typically containing air, body fluids and solid debris, is created in the main inlet 107. At the same time, air from the surrounding atmosphere enters the body 103 through orifices 101, 102 and merges with the main stream 108 to exit the device at outlet 104 as mixed fluid stream 109.

Should the inlet of tip 106 be blocked by contact with body tissues for instance, the thereby modified ratio between the tip inlet effective cross-section and that of the bypass orifices 101, 102, will automatically cause more air to be drawn through these orifices to prevent sudden increase of suction rate at the tip and firm grabbing of the tissues. However, air penetrating at high velocity through the small orifices in the inner chamber of the body 103 experiences turbulence due to rapid expansion at the inner side of the orifices and sharp edges at the interface between the inner chamber of the body 103 and the outlet portion 104. Turbulence creates acoustic waves tuned by the resonant cavity provided by the inner chamber, thus generating a hissing noise.

Other examples of such vented medical aspirators are described in U.S. Pat. No. 5,425,637 (Whitehouse et al.—June 1995), U.S. Pat. No. 5,509,802 (Whitehouse et al.—April 1996), U.S. Pat. No. 5,542,929 (Laabs et al.—August 1996) and U.S. Pat. No. 5,964,733 (Laabs et al.—October 1999).

Noise in medical aspirators, particularly dental aspirators used extensively and repeatedly by dentistry personnel, is recognized as a very significant problem. Indeed, it is a source of fatigue, stress accumulation and it represents a real risk of hearing acuity degradation for medical personnel. This noise problem has been specifically addressed in U.S. Pat. No. 5,195,952 issued to Solnit et al. in March 1993 which introduces the Grab Free™.

As illustrated in FIG. 5, the Grab Free™ is a device 100 which includes a plurality of tiny elongated bypass ports 111, 112 in the solid body 113. The body 113 includes an outlet portion 114 and an inlet portion 115 with a lip 116 for insertion of a removable suction tip. The main fluid which flows from the suction tip enters the main inlet 117 which has a constant cross-section port up to the outlet of the device. Upon clogging of the main inlet, air is drawn through the bypass ports and merges smoothly with the main flow due to the acute angle of incidence. Therefore, fluid streams follow smooth paths and merge as combined flow 119 at the outlet of the device with minimal separation, turbulence and resonance, leading to a significantly reduced noise level. However, the concept of this device provides fixed vacuum compensation and does not allow the user to block one or more of bypass ports 111, 112 to control the aspiration rate at the tip. Also, the weight of the solid metal body 113 at the downstream end of the device 110 adds to that of the vacuum hose and connector to create a moment of rotation about the user's wrist, yielding physical fatigue and discomfort of the user, to compensate the lift of the aspiration tip.

Suction control is indeed a desirable feature in aspirators used in dentistry as well as in many medical fields related to surgery, in lipectomy surgery or draining of wound fluids for instance. One may thereby avoid subjecting delicate tissues to too strong a suction force while properly performing aspiration of specific matters as needed. Therefore, some aspirator systems of the prior art justify and describe suction control or regulator devices of two types. In a first type, a venting port of relatively small effective area can selectively be either left open to provide a definite level of suction or blocked by a sleeve or a finger to momentarily increase suction, or vice versa. U.S. Pat. No. 4,534,542 (Russo—August 1985), U.S. Pat. No. 5,855,562 (Moore et al.—January 1999), U.S. Pat. No. 5,975,897 (Propp et al.—November 1999) and U.S. Pat. No. 6,045,516 (Phelan—April 2000), as well as Canadian patent No 2,042,523 (Nates—Oct. 1995) exemplify that first type of controlled vacuum aspirators.

Fewer suction control devices of a second type are so designed to enable a user to continuously vary suction over a given range. Representative examples of aspirators implementing such suction control devices are described in U.S. Pat. No. 4,221,220 (Hansen—September 1980), U.S. Pat. No. 5,013,300 (Williams—May 1991), U.S. Pat. No. 5,730, 727 (Russo—March 1998), U.S. Pat. No. 5,899,884 (Cover et al.—May 1999) and U.S. patent application No. 2002/0108614A1 filed by Schultz in April 2002.

The published patent application by Schultz, which is illustrated in FIG. 6, teaches a hand-held medical component which is provided with a wide elongated port for regulating suction. Suction is provided from a device which comprises a body 123 with an inlet portion 125 and an outlet portion 124 for connection to a vacuum source. The device is further provided with a large opening and relatively large throat bypass inlet penetrating the body up to the inner chamber 122. The large elongated opening of the bypass inlet 121 is so designed as to enable a user to control the suction rate at the inlet of suction tube 126 by selectively blocking a variable portion of said opening with a finger. Although such a feature is highly desirable in many applications, noise with such a device is still a major problem which prevents its extensive use in applications such as dentistry. Indeed, the main fluid stream 128 rapidly expands and separates when passing from the inlet 125 to the chamber 122 of much larger cross-sectional area. Similarly, the pressure compensating air flow penetrating the chamber from inlet 121, experiences separation and turbulence due to the orthogonal incidence when merging into the main stream and to the sharp edges present at the interface. Therefore, the main and bypass flows could not merge to form an outlet fluid stream 129 without generating a highly noisy acoustic emission tuned according to the dimensions of chamber 122 and because of the resonant cavity yielding flow separation, turbulence, acoustic amplification and, consequently, intense irritating noise.

With the exception of the Solnit Patent, all of the aforementioned patents have their bypass inlet extending straight through the outer wall of the aspirator body such that the incoming airflow substantially forms a right angle with respect to the fluid stream in the main bore of the device. Also, none of the auxiliary aperture shapes have been specifically designed in consideration of the aero-acoustic concerns for optimal merging of the bypass air flow from atmosphere with the main fluid stream, that is with minimal energy being dissipated and converted into sound waves, and minimal transfer of said sound waves to the surrounding work environment.

Although the above examples show that some suction control bypass devices and controlled aspirating devices are contemplated in the prior art, these devices are nevertheless lacking important features necessary for them to provide adequate control of aspiration rate as required in medical applications for instance, while generating low level minimally annoying noise.

It would therefore be a significant advance in the art of controlled suction aspirating devices to provide a low-noise suction control device and an aspirator using such a device, which can be advantageously controlled with a user's finger or sliding sleeve to provide a wide range of aspiration rates, while generating low and minimally annoying noise, according to preferred structures as contemplated in the present invention. It would also be desirable to provide an aspirator which enhances the physical comfort of a user through an ergonomic design providing weight balance and natural and adjustable tip angulations.

OBJECTS OF THE INVENTION

An object of the present invention is therefore to provide a low-noise aspiration control port and an aspirator using same.

SUMMARY OF THE INVENTION

More specifically, in accordance with the present invention, there is provided a suction device for an aspirator connectable to a vacuum source, the suction device including a body including an external surface, an inlet port located at a first end of the body, an outlet port located at a second end of the body, a chamber extending inside the body from the inlet port to the outlet port along a longitudinal axis, the chamber defining a flow direction from the inlet port to the outlet port, the suction device further including a bypass inlet diverging through the body from the external surface to the chamber generally along the flow direction.

There is furthermore provided a suction device for an aspirator connectable to a vacuum source, the suction device including a body including an external surface, an inlet port located at a first end of the body, an outlet port located at a second end of the body, a chamber defined by a diverging portion from the inlet port to a junction position and a converging portion from the junction position to the outlet port, a bypass inlet extending through the body from the external surface in the vicinity of the inlet port to the chamber in the vicinity of the junction position.

There is furthermore provided a suction device for an aspirator connectable to a vacuum source, the suction device including a body including an external surface, an inlet port provided in the vicinity of a first end of the body, an outlet port provided in the vicinity of a second end of the body, a chamber extending inside the body from the inlet port to the outlet port along a longitudinal axis, the chamber defining a flow direction from the inlet port to the outlet port, the suction device further including a bypass inlet extending through the body from an elongated aperture on the external surface to the chamber and at an acute angle with respect to the flow direction.

There is furthermore provided a suction system for an aspirator connectable to a vacuum source including a suction device including a body including an external surface, an inlet port located at a first end of the body, an outlet port located at a second end of the body, a chamber extending inside the body from the inlet port to the outlet port along a longitudinal axis, the chamber defining a flow direction from the inlet port to the outlet port, the suction device further including a bypass inlet extending through the body at an acute angle with respect to the flow direction from an outer aperture on the external surface of the body to an inner aperture in the chamber, the suction system further including a control means operatively mounted over the outer aperture for blocking the bypass inlet, whereby upon operation of the vacuum source sealingly mounted to the outlet port, a first suction force is generated at the inlet port and a second suction force is generated at the bypass inlet, the first suction force being variable upon actuation of the control means.

There is furthermore provided an aspirator connectable to a vacuum source for aspiring particles and or fluids including a suction device including a body including an external surface, an inlet port located at a first end of the body, an outlet port located at a second end of the body, a chamber extending in the body along a longitudinal axis from the inlet port to the outlet port, and a bypass inlet diverging through the body from the external surface to the chamber, whereby upon operation of the vacuum source sealingly mounted to the outlet port, a first suction flow is generated at the inlet port and a second suction flow is generated at the bypass inlet such that the first suction flow and the second suction flow combine in the chamber near the inner aperture.

It is to be noted that the expression vacuum source is to be construed herein and in the appended claims as a system which is independently capable of generating a negative pressure inducing a suction flow or an aspiration line in the vicinity of the system, while in operation.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

In the appended drawings:

FIG. 1 is a top view of the suction device according to an embodiment of the present invention;

FIG. 2 is a cross sectional view taken along line 2-2 of FIG. 1;

FIG. 3 is a detail view of a bypass inlet taken from enclosure 3-3 of FIG. 2;

FIG. 16 is a comparative chart representing the noise level generated by the suction device of the present invention and by three suction devices of the prior art.

DETAILED DESCRIPTION

Generally stated, the present invention relates to a vacuum release or suction device 20, as illustrated in FIGS. 1, 2 and 3, for controlling the suction rate in an aspiration line with minimal generated aerodynamic noise. The invention further relates to a hand-held aspirator of the type used for medical purposes, such as for aspirating body fluids from a patient, saliva, water, blood and debris from a patient's mouth during a dental treatment or surgery, for example. The contemplated aspirator may be controllable and is provided with a low noise suction device 20 of the present invention.

Figure 4:
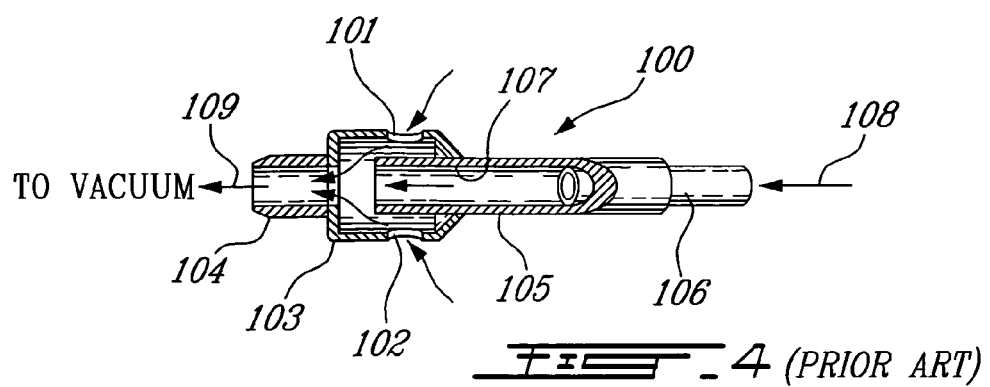
FIG. 4, which is labeled "prior art", is a longitudinal cross sectional view showing a first prior art suction device.
Figure 5:
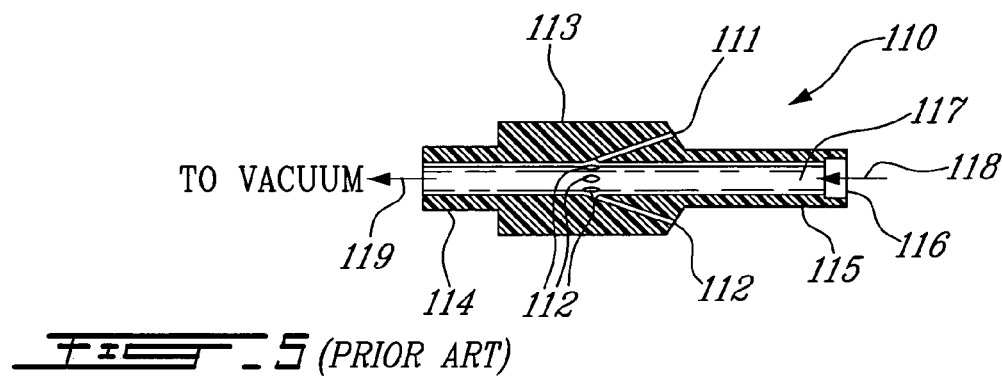
FIG. 5, which is labeled "prior art", is a longitudinal cross sectional view showing a second prior art suction device.
Figure 6:
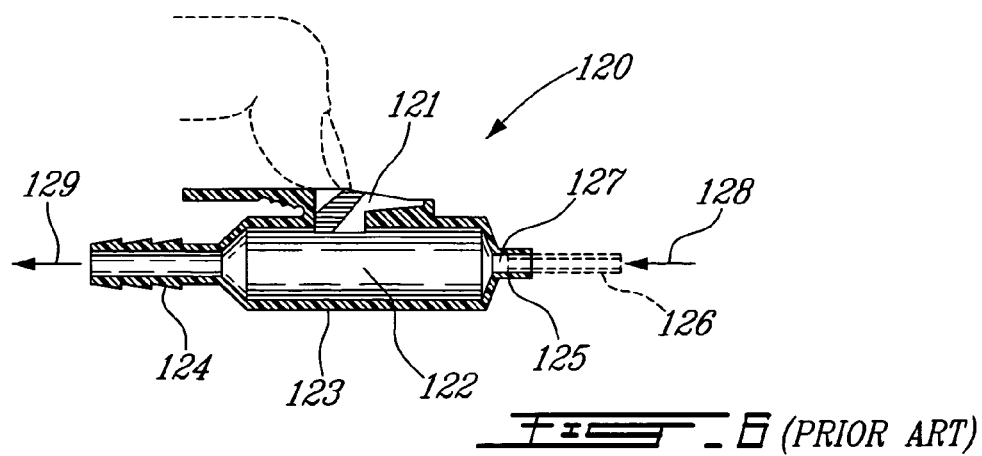
FIG. 6, which is labeled "prior art", is a longitudinal cross sectional view showing a third prior art suction device.

Examples of prior art aspirators having suction capabilities are illustrated in FIGS. 4 to 6.

The device 20 according to an embodiment of the present invention will be described.

The device 20 has a body 22 including a first end or main inlet portion 24 and a second end or main outlet portion 26. The main inlet portion 24 has an inlet port 28 which is so configured as to be mounted to an aspirating tool and may comprise a ridge 30, a groove (not shown) retaining a "O" ring seal member (not shown), or another positive coupling mechanism to attach tooling or extension tubing in a substantially fluid tight manner. The main outlet portion 26 has an outlet port 32 which is so configured as to be mounted to a vacuum source (not shown).

The body 22 of the device further includes a chamber 34 which is provided between the inlet port 28 and the outlet port 32; and a bypass inlet 36 which generally extends through the body 22, such that it connects or opens the chamber 34 to the atmosphere. As can be better seen in FIG. 1, the bypass inlet 36 diverges while traversing the body from the external surface of the body 22 to the chamber 34 (see reference numeral 39 indicating the walls of the bypass inlet 36). The bypass inlet 36 therefore becomes larger as it approaches the chamber 34 and the bypass inlet 36 is done through the body 22 generally along the flow direction 42 as can be better seen in FIG. 2.

The chamber 34 is made of two generally frusto-conical portions 38, 40, such that the cross-sectional area of the chamber 34 gradually increases from the inlet port 28 to the vicinity of the bypass inlet 36 and then gradually decreases toward the outlet port 32. This arrangement favors a smooth merge of a generally quasi laminar main flow 42 entering the inlet port 28 and a bypass flow 44 entering the bypass inlet 36 to constitute a combined outlet stream 45.

The first generally smooth and diverging frusto-conical portion 38 extends from the vicinity of inlet port 28 and generally up to the vicinity of the connection of the chamber 34 with the bypass inlet 36, therefore providing a gradual increase of the cross-sectional area of the chamber 34.

This arrangement generally provides some velocity reduction of the main flow 42, while minimizing the risks of sudden changes of flow direction and thus turbulence, particularly in the region of the bypass inlet 36 and to promote the merging of both flows 42, 44 in laminar or nearly laminar conditions.

The second generally smooth and converging frusto-conical portion 40 extends from the vicinity of the connection of the chamber 34 with the bypass inlet 36 to the vicinity of the outlet port 32.

The ramping angle θi of the inlet frusto-conical portion 38 is advantageously selected between about 2 and about 7 degrees, with a preferred value of about 3.5 degrees with respect to chamber 34 longitudinal axis 46, while the ramping angle θo of the outlet portion 40 is advantageously selected between about 3 and about 10 degrees, with a preferred value of about 7 degrees.

As can be better seen from FIG. 3, the bypass inlet 36, which extends through the body 22 of the device 20, generally includes a lower ramp or surface 48, an upper ramp or surface 50, an outer aperture 52 and an inner aperture 54. The bypass inlet 36 also includes a lip 56 near the outer aperture 52 and may adopt various configurations as it extends through the body 22.

One example illustrating an extending configuration for a bypass inlet 36 is shown in FIGS. 1, 2, 3, 7 and 8. This configuration is inspired from a profile known in the field of aeronautics as a "NACA inlet", which has been specifically developed and optimized by the National Advisory Committee for Aeronautics, predecessor of the modern day NASA, to enable air flow to enter a body with minimal flow separation and turbulence. Reader may refer to NACA's research memorandum entitled "An Experimental Investigation of the Design Variables for NACA Submerged Duct Entrances" By Mossman et al. (Jan. 8, 1948) for a detailed teaching of the subject. This document is included herein by reference in its entirety.

In this configuration, the outer aperture 52 of the bypass inlet 36 has a shape or contour which is generally flush with outside surface of the body 22 and the bypass inlet 36 is generally submerged in the body 22. The contour of the outer aperture 52 is shown in FIG. 7 and may be defined according to the table of coordinates provided in FIG. 8, for example.

Figures 7, 8:
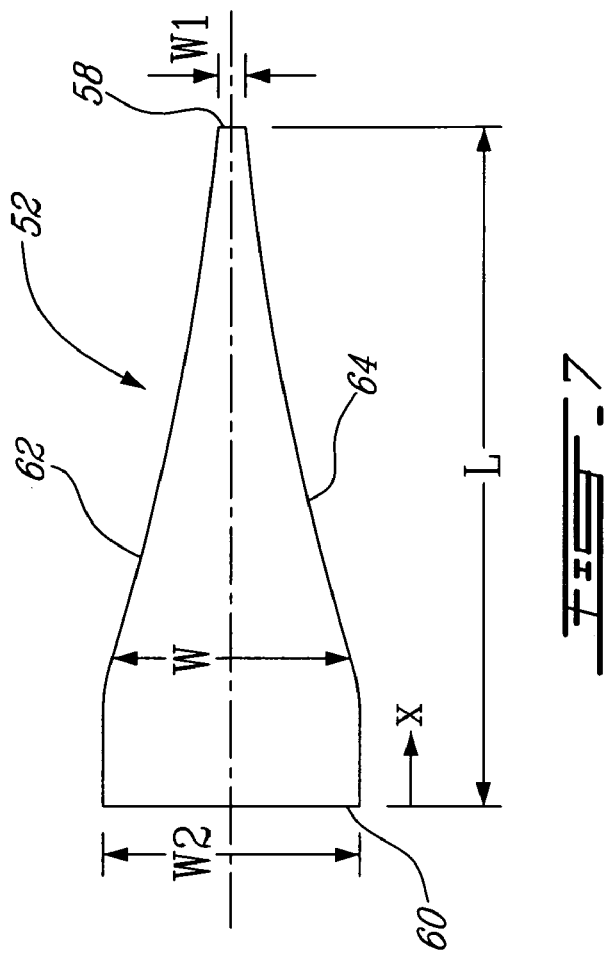
FIG. 7 is a top view showing an outer aperture contour of the suction device of FIG. 1.
FIG. 8 is a table including the contour parameters of the outer aperture shown in FIG. 7.

More specifically, as can be seen from FIG. 7, the outer aperture 52 generally includes a narrow end 58 of width W1 at its upstream end (nearer to the inlet portion 24 of the device 20) and a wide end 60 of width W2 forming the lip 56 at its opposite downstream end (nearer to the outlet portion 26 of the device 20). Ends 58 and 60 are generally connected by curvilinear lateral edges 62, 64 which are being defined in the Table of FIG. 8, given the width of the outer aperture 52 at given values of longitudinal position x. The edges 62, 64 can also be approximated by linear edges, forming a nearly triangular inlet. The overall length L of the outer aperture 52 is generally larger than width W2, which is larger than W1.

W1 generally ranges from about 0 to about 20 millimeters, with a preferred value of about 0.8 millimeters, and W2 generally ranges from about 5 millimeters to about 25 millimeters with a preferred value of about 10 millimeters, and the length L generally ranges from about 10 millimeters to about 50 millimeters, with a preferred value of about 30 millimeters.

Returning to FIG. 3, to direct the flow of air 44 from the bypass inlet 36 toward the outlet of chamber 34 with an acute incidence angle of about 3 to about 10 degrees, with a preferred value of about 7 degrees, the lower ramp 48 and the upper ramp 50 respectively form an angle $\alpha L$ and an angle $\alpha U$ ranging from about 3 degrees to about 10 degrees with respect to the longitudinal axis 46 of the chamber 34, with a preferred value of about 7 degrees. Ramps 48, 50 may be substantially parallel (about same angle $\alpha L$ and $\alpha U$), or may slightly diverge toward the inner aperture 54. The lower ramp 48 and the upper ramp 50 of the bypass inlet 36 may be spaced by a distance ranging from about 1 to a bout 5 millimeters, with a preferred value of about 2.65 millimeters, as measured on a transversal axis (not shown) which is generally orthogonal to the longitudinal axis 46 of the chamber 34.

Further, the lip 56 is designed to provide a smooth transition from the external surface of the body 22 to the bypass inlet 36 in order to minimize airflow separation and resulting turbulence.

Figures 9, 10:
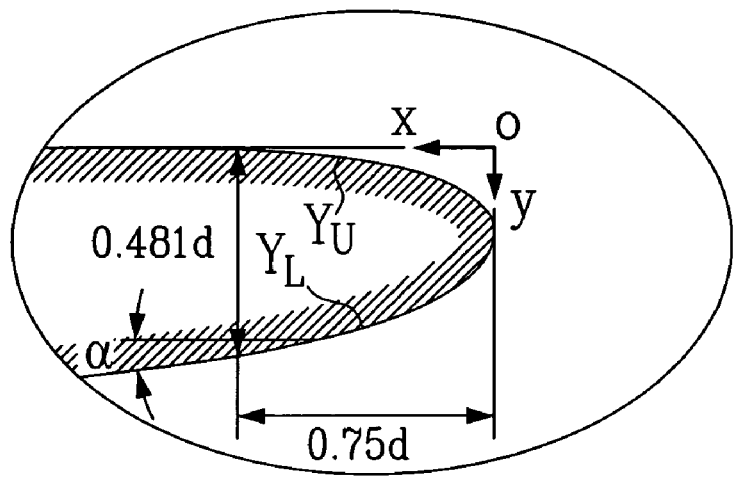
FIG. 9 is a detail view of a lip contour taken from enclosure 9-9 of FIG. 3.
FIG. 10 is a table including the contour parameters of the lip of FIG. 9.
Figure 11:
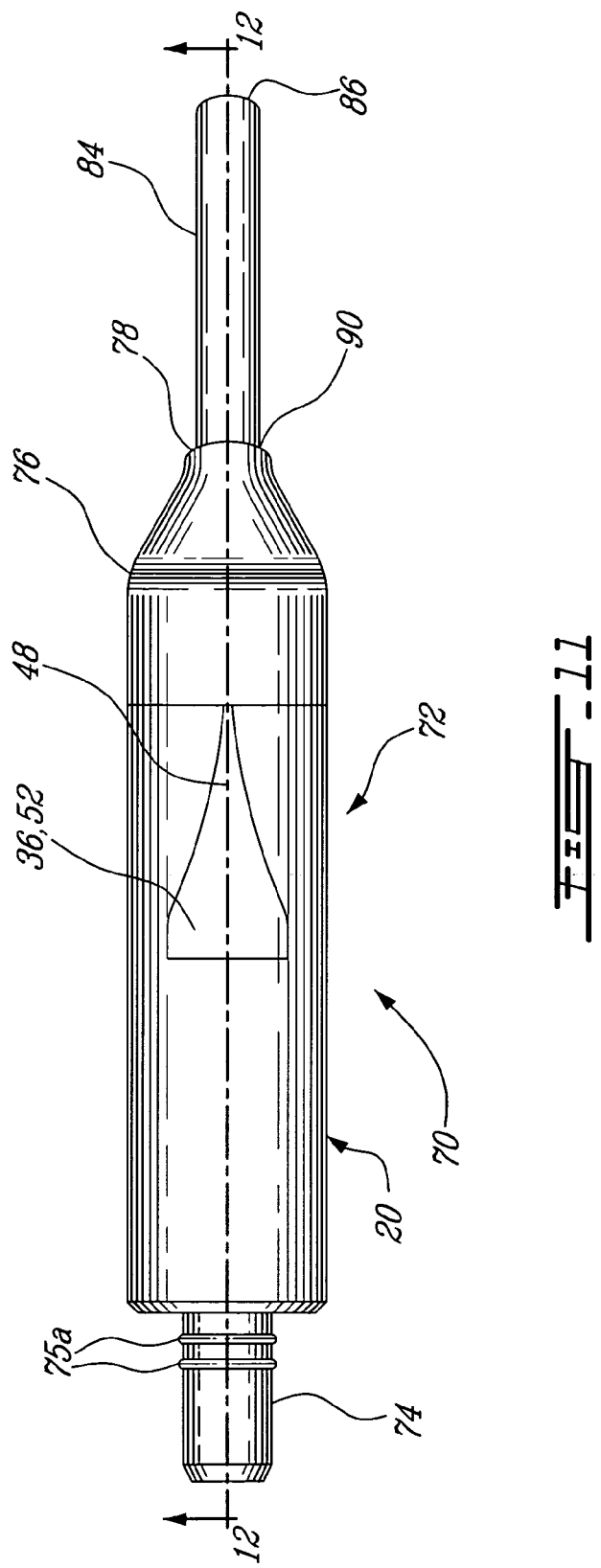
FIG. 11 is a top view of an aspirator equipped with a suction device according to the present invention.

A possible shape of the lip 56 is illustrated in FIG. 9 and defined in the table of FIG. 10, wherein the values of the positions of the upper edge Yu and lower edge Yl are provided for given values of the longitudinal displacement x, as a function of d, which is the vertical distance between the upper and the lower ramps 48, 50 (FIG. 3) and which is calculated as follows from equation (A):

$$d = L\ tg\ \alpha/[1.481 - 0.75\ tg\ \alpha] \quad (A)$$

where $\alpha$ is the ramp angle ($\alpha = \alpha L = \alpha U$) and L is the overall length of the outer aperture 52, as illustrated in FIG. 7. A smooth transition at the entrance of lower ramp 48 is also contemplated to prevent flow separation, such that the radius of curvature r shown in FIG. 3 should not be much smaller than about 5 millimeters.

The design of the bypass inlet 52 is so configured as to provide minimum flow separation and turbulence as required to reduce the generated aero-acoustic noise. Turning back to FIG. 2, the vacuum source of the suction device 20 while in operation creates a negative pressure, i.e. suction, at the outlet port 32, which in turn causes main flow 42 and bypass flow 44 to be drawn respectively from the main inlet port 28 and the bypass inlet 36 to merge at a junction position 54a near the inner aperture 54, to constitute the combined outlet stream 45. The bypass flow 44 is generally constituted from surrounding atmospheric air while main flow 42 may comprise a mixture of air, gases, liquids and solid matters to be extracted from a location using a suction tool to be connected to inlet portion 24.

The flows of fluid through main inlet port 28 and bypass inlet 36 are generally a function of the applied vacuum intensity and of the resistance to flow resulting from each inlet/bore characteristics. One of the characteristics determining flows of fluid is the effective cross-section and duct length of the inlet ports 28, 36. Therefore, for given characteristics of the main inlet port 28 and suction tooling connected thereto, such as for example a rotary adapter and suction tip (not shown), modifying the effective area of the outer aperture 52 of the bypass inlet 36 modifies suction, i.e. flow and maximum pressure at the main inlet port 28. The area of the outer aperture 52 is thus designed to define minimum desired values for the flow and pressure at the main inlet port 28. In use, it is possible for a user to partly or totally block bypass inlet aperture 52, with a finger, with part of a hand, or with any other blocking element to increase suction to a desired value as necessary at any time of an operation.

A user may also merely block a portion of the relatively large bypass inlet aperture 52 with a finger or alternatively, using a control means in the form of a sliding sleeve (not shown) to continuously control suction between a minimum and a maximum value. The optional use of a sleeve (not shown) may be useful to minimize direct contact of the users gloved skin with the fluid and matters flowing through the device 20, which could present risks of contamination or injury, although the current design of the preferred embodiment advantageously minimizes such contact.

The device 20 which was described hereinabove may be used in a variety of applications, such as for example in a dentistry aspirator to extract debris along with water, saliva, blood and air from a patient's mouth. Such an embodiment is illustrated at FIGS. 11 through 15.

The low-noise suction device or aspirator 70 includes a central portion 72 including a low-noise vacuum release or suction device 20 as described above. The main outlet portion 26 may include a female configuration which may be connected to a removable male adapter 74. The male adapter 74 may be selected to be mounted to a variety of vacuum hoses, valves or other connection devices (not shown). Press-fit assembly or "O" rings 75a co-operating with grooves 75b may be contemplated to provide a substantially fluid tight connection.

Figure 14:
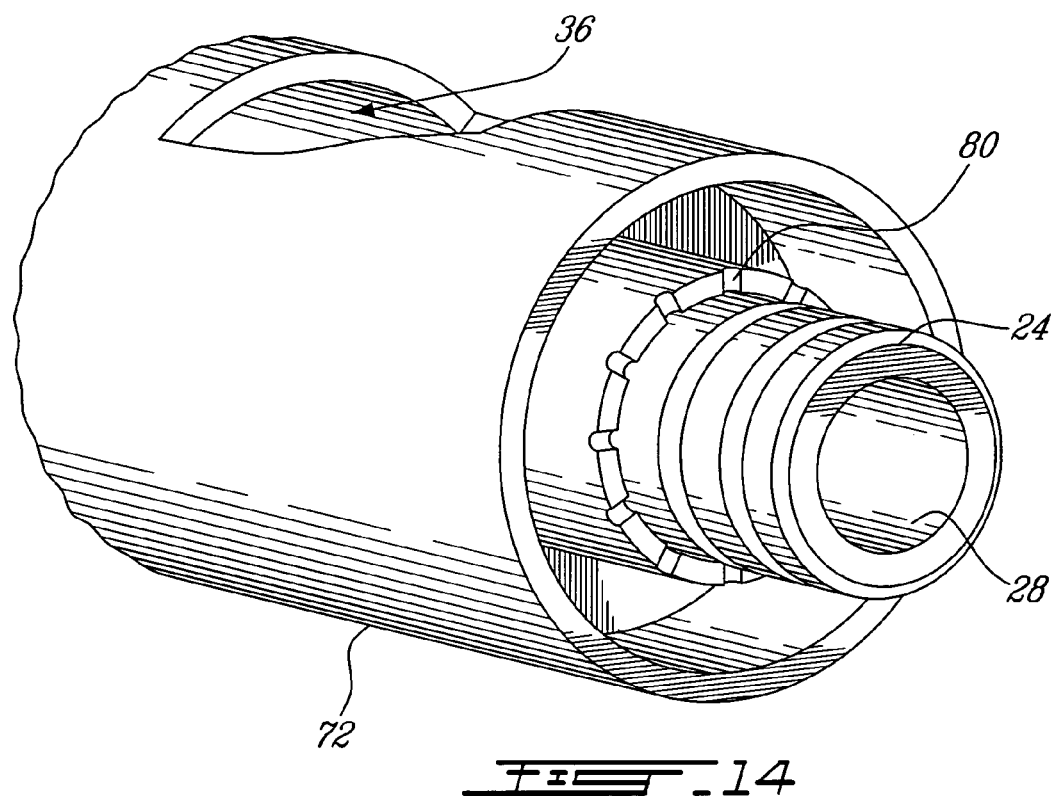
FIG. 14 is a partial isometric view of the suction device included in the aspirator of FIG. 11.
Figure 15:
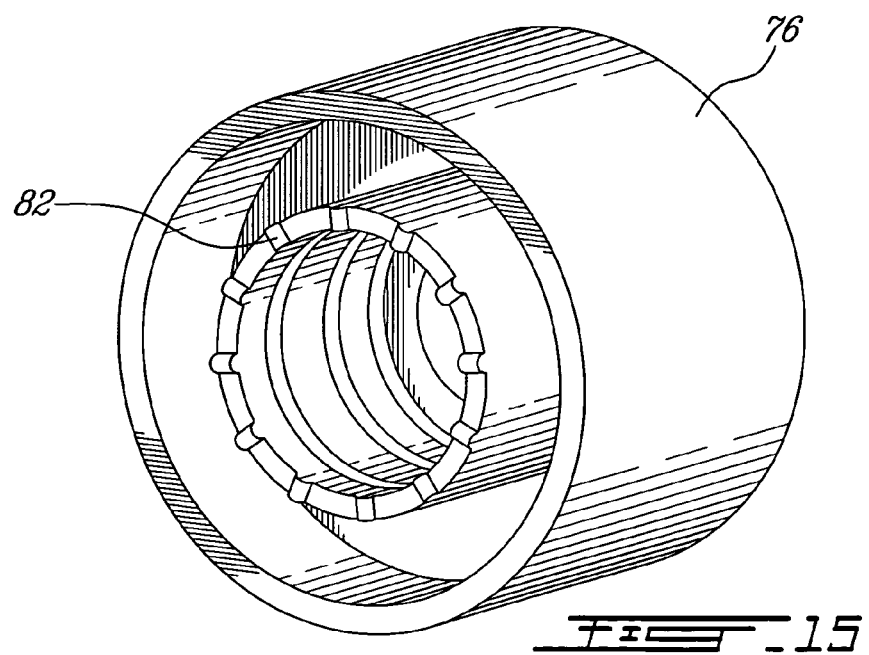
FIG. 15 is a partial isometric view of the tool adapter included in the aspirator shown of FIG. 11.

At the fore (upstream) end of the aspirator 70, a tool adapter 76, which is provided with an angular tool holding inlet portion 90, is assembled over the main inlet portion 24 for rotation about the longitudinal axis of the aspirator 70. An indexing mechanism, as shown in FIGS. 14 and 15, such as for example mating notches and ridges located on surfaces 80 and 82 of the aspirator 70 and tool adapter 76 respectively, are provided to positively set and maintain the angular position of the tool adapter 76 to a user selected comfortable position. A fluid tight rotary joint using "O" rings or ridges (not shown) on the main inlet portion 24 with or without mating grooves (not shown) inside the bore of the tool adapter 76 may alternatively be used, without any step indexing mechanism, in order to enable continuous full 360 degrees rotation of the tool adapter 76 about the aspirator 70 longitudinal axis. A hollow suction tip 84 comprising an inlet 86 and an outlet 88 is removably inserted in the inlet 90 of the angular tool holding portion 78.

Figure 12:
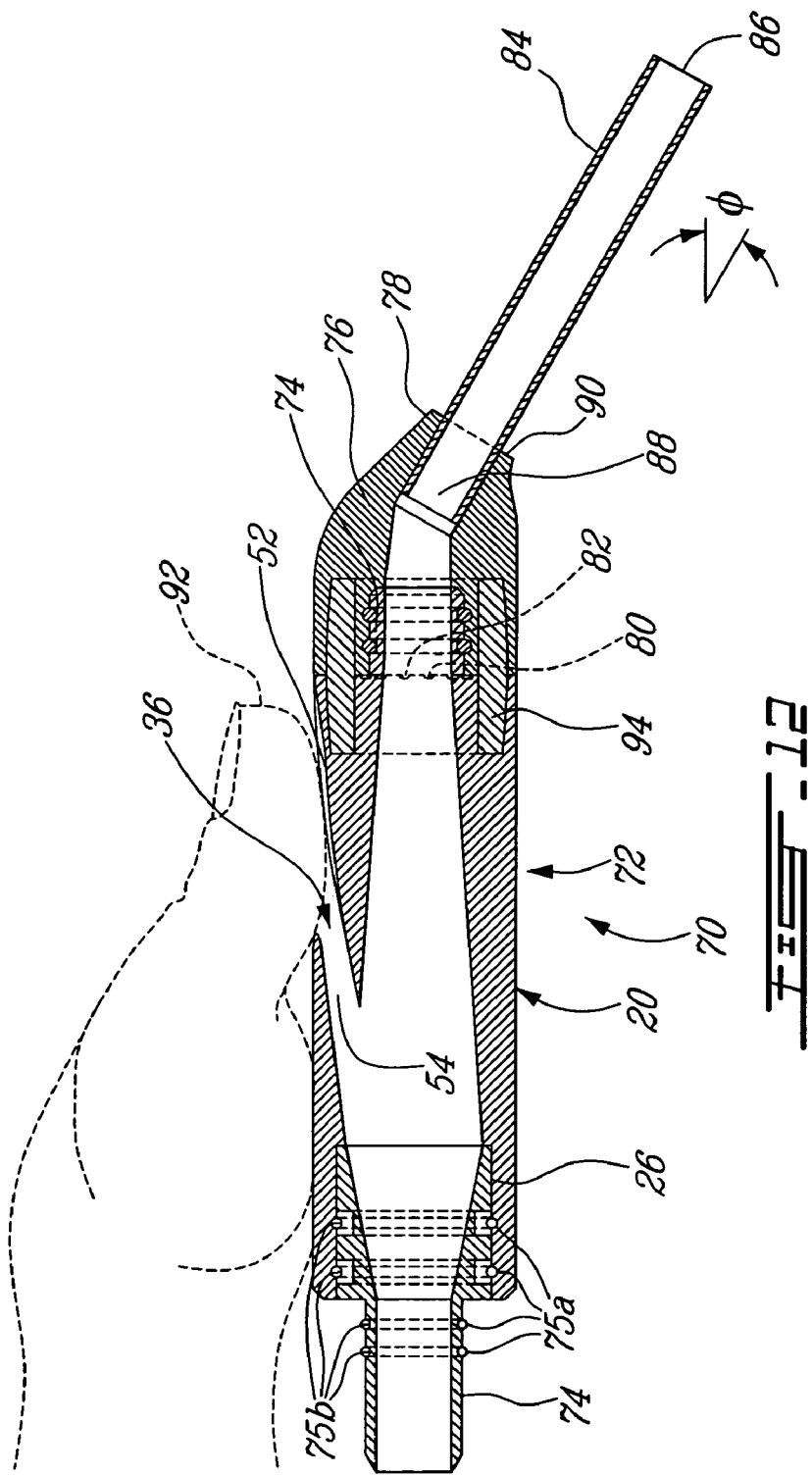
FIG. 12 is a cross sectional view taken along line 12-12 of FIG. 11.
Figure 13:
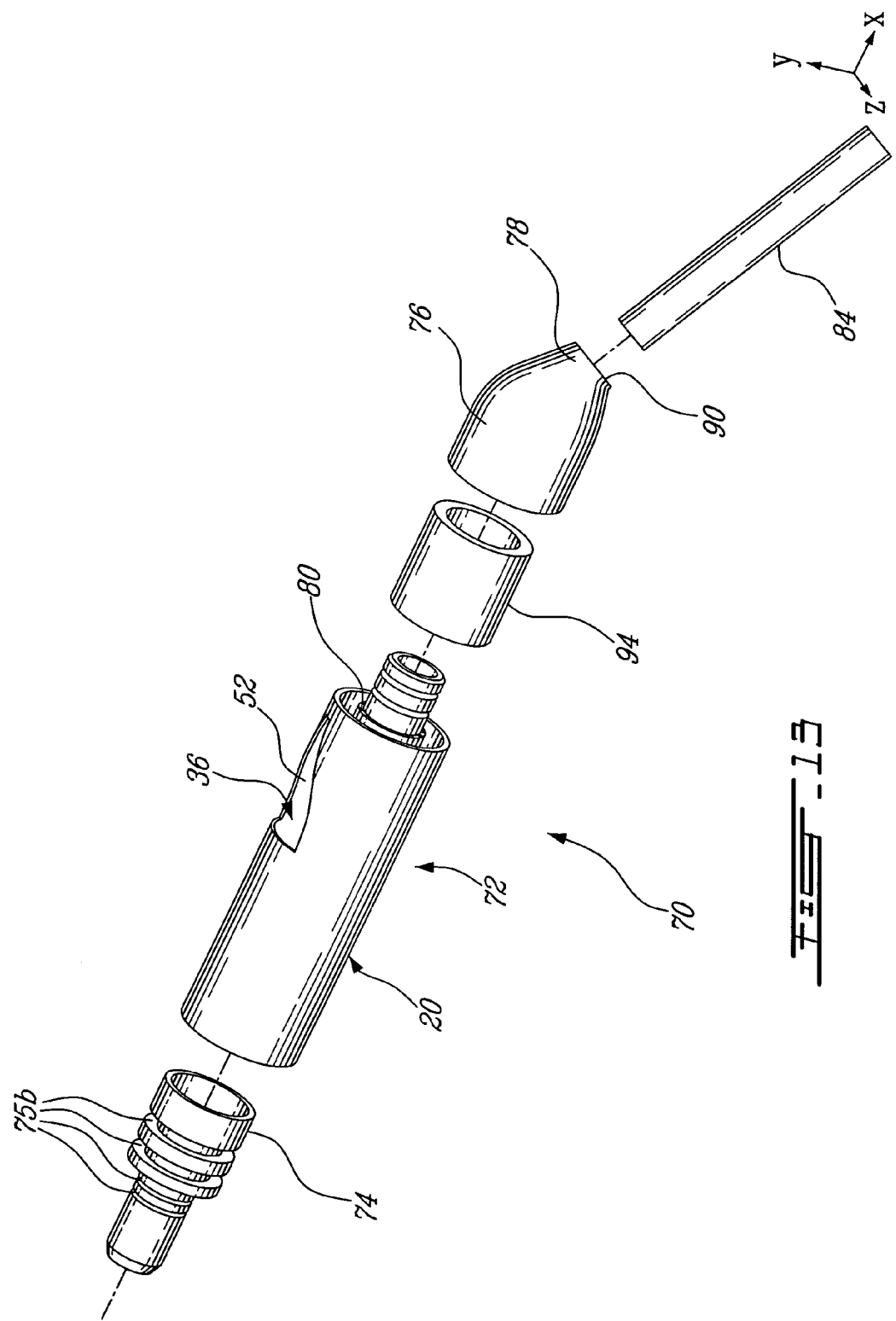
FIG. 13 is an isometric exploded view of the aspirator of FIG. 11.

From FIG. 12, it can be seen that the user may use one's thumb 92 to vary the effective area of the bypass inlet 36 to modify suction at the inlet 86 of suction tip 84. In addition, part of the volume between the outer shell of the tool adapter 76 and its central bore is filled with a dense material such as for example a stainless steel bushing 94, to increase the weight at the fore end of the aspirator 70, thus improving balance and reducing stress and fatigue in the user's wrist by causing a displacement of the centre of gravity of the aspirator 70.

For dentistry applications, the angle φ of orientation of the tool holding portion 78 with respect to a longitudinal axis of the aspirator 70 is generally set between about 10 and about 45 degrees, with a preferred value of about 30 degrees. The tool adapter 76 may be further provided with a revolving means (not shown), for adjusting the angular orientation of the suction tip 84 about the longitudinal axis of the aspirator 70.

In such an application, a suction force ranging from about 35 to about 70 grams at tip inlet 86 is considered most desirable when the outer aperture 52 of the bypass inlet 36 is fully open, with a preferred value of about 70 grams. The maximum suction force generated by the aspirator 70 in the fully closed bypass inlet configuration is about 180 grams with about 250 millimeters Hg suction pressure applied to the aspirator 70. This is achieved with a suction inlet cross-section of about 47 square millimeters at tip inlet 86 and a bypass cross-sectional area of about 27 square millimeters at inner aperture 54. Accordingly, dimensions of the external bypass aperture 52 of an exemplary device are as follows:

10 millimeters<L<50 millimeters;
5 millimeters<W2<25 millimeters; and
0 millimeters<W1<20 millimeters.

In an example, a prototype having the following dimensions was constructed, L=30 millimeters, W2=10 millimeters and W1=0.8 millimeters, leading to a calculated value of d=2.65 millimeters. To prevent flow separation, radius of curvature r at the entrance of the lower ramp 48 (see FIG. 3) should be between about 2 millimeters and about 50 millimeters with a preferred value of about 7.5 millimeters.

FIG. 16 provides a graphical comparison of the various levels of noise generated by the use of the three prior art aspirators which were shown in FIGS. 4 to 6 and by the prototype aspirator 70 including a suction device 20 of the present invention. As seen in this Figure, the total acoustic power emitted by the prototype, connected to a 250 millimeters Hg vacuum line through a US standard connection and with its bypass inlet 36 fully open, is about 5 db less than that of the Grab Free™ aspirator in the same condition, 12 db less than the Tip-A-Dilly™ aspirator in the same condition and 14 db less than the aspirator commercialized by the Siemens company with its European connection. The reader is reminded that a 5 db difference in acoustic power represents a reduction of more than 68% of the acoustic energy, and that a 10 db difference represents a 90% reduction of acoustic energy emission.

In addition to these sonometric results, listening tests also revealed that the noise generated by the aspirator 70 prototype was considered by listeners to be far less irritating due to its different spectral distribution especially in the 1000 Hz to 6000 Hz range. This is mainly due to the much lower intensity at higher frequencies of the audio spectrum, while the higher levels recorded in the lower end result in an almost pleasant humming type of noise. It has to be noted that medical research shows that the human ear is most sensitive to frequencies comprised in the high and shrill 1000 Hz to 6000 Hz range.

One can easily appreciate that the above described embodiments according to the present invention provide effective solutions for the reduction of noise in suction devices while providing the user with a wide range of suction control. Therefore, it can be seen that the low-noise vacuum release suction device and the controllable aspirator provided with such a suction device can be advantageously used in miscellaneous suction applications, and more particularly in dentistry, to reduce the stress experienced by the personnel due to noise.

Although the present invention has been described hereinabove by way of preferred embodiments thereof, it can be modified, without departing from the spirit and nature of the subject invention as defined in the appended claims.

What is claimed is:

1. A suction device for an aspirator connectable to a vacuum source, said suction device comprising:
   a) a body including an external surface;
   b) an inlet port located at a first end of said body;
   c) an outlet port located at a second end of said body;
   d) a chamber extending inside said body from said inlet port to said outlet port along a longitudinal axis; said chamber defining a flow direction from said inlet port to said outlet port; and
   e) a bypass inlet diverging through said body from said external surface to said chamber generally along the flow direction.

2. A suction device as recited in claim 1, wherein said bypass inlet extends through said body at a predetermined angle with respect to said longitudinal axis.

3. A suction device as recited in claim 2, wherein said predetermined angle is acute with respect to said longitudinal axis.

4. A suction device as recited in claim 1, wherein said longitudinal axis extends along the flow direction.

5. A suction device as recited in claim 1, wherein said chamber includes a diverging portion generally extending from said inlet port to said bypass inlet, and a converging portion extending from said bypass inlet to said outlet port.

6. A suction device as recited in claim 5, wherein said diverging portion and said converging portion are generally frusto-conical.

7. A suction device as recited in claim 5, wherein said diverging portion ramps at an angle which ranges from about 2 to about 7 degrees with respect to said longitudinal axis.

8. A suction device as recited in claim 5, wherein said converging portion ramps at an angle which ranges from about 3 to about 10 degrees with respect said longitudinal axis.

9. A suction device as recited in claim 1, wherein said bypass inlet includes a lower ramp and an upper ramp extending through said body; said lower and upper ramps defining an inner aperture and an outer aperture; said outer aperture diverging on said external surface along said flow direction.

10. A suction device as recited in claim 9, wherein said diverging outer aperture of said bypass inlet is bounded by curvilinear lateral edges.

11. A suction device as recited in claim 9, wherein said lower ramp and said upper ramp extend at an acute angle with respect said longitudinal axis.

12. A suction device as recited in claim 11, wherein said acute angle ranges from about 3 to about 10 degrees.

13. A suction device as recited in claim 9, wherein said lower ramp and said upper ramp diverge from each other from said outer aperture to said inner aperture.

14. A suction device as recited in claim 9, wherein said lower ramp and said upper ramp are substantially parallel.

15. A suction device as recited in claim 9, wherein said bypass inlet includes a lip located at a junction between said outer aperture and said upper ramp.

16. A suction device as recited in claim 9, wherein said bypass inlet includes a rounded junction between said outer aperture and said lower ramp.

17. A suction device as recited in claim 9, wherein said bypass inlet has a "NACA inlet" configuration.

18. A suction device as recited in claim 1, wherein said device further includes a sleeve slidably mounted over said body and in the vicinity of said bypass inlet to control the suction at said bypass inlet.

19. A suction device for an aspirator connectable to a vacuum source, said suction device, comprising:
   a) a body including an external surface;
   b) an inlet port located at a first end of said body;
   c) an outlet port located at a second end of said body;
   d) a chamber comprising a cross-section defined by a diverging portion from said inlet port to a junction position and a converging portion from said junction position to said outlet port; and
   e) a bypass inlet extending through said body from said external surface in the vicinity of said inlet port to said chamber in the vicinity of said junction position, wherein said bypass inlet diverges through said body from said external surface to said chamber.

20. A suction device as recited in claim 19, wherein said bypass inlet extends through said body at an acute angle with respect to a longitudinal axis of said chamber.

21. An aspirator connectable to a vacuum source for aspiring particles and or fluids comprising:
   a suction device including:
      a) a body comprising an external surface;
      b) an inlet port located at a first end of said body;
      c) an outlet port located at a second end of said body;
      d) a chamber extending in said body along a longitudinal axis from said inlet port to said outlet port; and
      e) a bypass inlet diverging through said body from an outer aperture in said external surface to an inner aperture in said chamber;
whereby upon operation of the vacuum source sealingly mounted to said outlet port, a first suction flow is generated at said inlet port and a second suction flow is generated at said bypass inlet such that said first suction flow and said second suction flow combine in said chamber near said inner aperture.

22. An aspirator as recited in claim 21, wherein said aspirator further includes a tool adapter comprising a passage defined between a first end sealingly mounted to said inlet port and a second end, said first suction flow being generated at said second end of said tool adapter.

23. An aspirator as recited in claim 22, wherein said aspirator further includes a hollow suction tip comprising an inlet and an outlet, said outlet being removably inserted in said second end of said tool adapter, said first suction flow being generated at said inlet of said suction tip.

24. An aspirator as recited in claim 22, wherein said aspirator and said tool adapter include an indexing mechanism to rotatably position said tool adapter with respect to said aspirator.

25. An aspirator as recited in claim 22, wherein said tool adapter is rotatably mounted to said inlet port through at least one ridge and groove arrangement.

26. An aspirator as recited in claim 22, wherein said tool adapter is sealingly mounted to said inlet port through at least one "O" ring joint.

27. An aspirator as recited in claim 22, wherein said tool adapter further includes an outer shell and a central bore defined between said first end and said second end, and a bushing made from a dense material and located between said shell and said bore.

28. An aspirator as recited in claim 21, wherein said aspirator further includes a removable adapter sealingly connectable to the vacuum source and to said outlet port.

29. An aspirator as recited in claim 28, wherein said removable adapter is mounted to said outlet port and to said vacuum source by a press-fit assembly.

30. An aspirator as recited in claim 28, wherein said removable adapter is mounted to said outlet port and to said vacuum source through at least one ridge and groove arrangement.

31. A suction system for an aspirator connectable to a vacuum source, comprising:
   a) a suction device including:
      i) a body including an external surface;
      ii) an inlet port located at a first end of said body;
      iii) an outlet port located at a second end of said body;
      iv) a chamber extending inside said body from said inlet port to said outlet port along a longitudinal axis; said chamber defining a flow direction from said inlet port to said outlet port, said chamber comprising a converging portion thereof; and
      v) a bypass inlet extending through said body at an acute angle with respect to the flow direction from an outer aperture on said external surface of said body to an inner aperture in said chamber, said bypass inlet merging into said chamber converging portion; and
   b) a control means operatively mounted over said outer aperture for at least partially blocking said bypass inlet;
wherein said converging portion is preceded by a diverging portion of said chamber, whereby upon operation of the vacuum source sealingly mounted to said outlet port, a first suction force is generated at said inlet port and a second suction force is generated at said bypass inlet, said first suction force being variable upon actuation of said control means.

* * * * *